US008217079B2

(12) United States Patent
Mascagni et al.

(10) Patent No.: US 8,217,079 B2
(45) Date of Patent: Jul. 10, 2012

(54) METHOD FOR TREATING PHILADELPHIA-NEGATIVE MYELOPROLIFERATIVE SYNDROMES

(75) Inventors: Paolo Mascagni, Villasanta (MI) (IT); Carmine D'urzo, Via Natta (IT); Joseê Golay, Bergamo (IT)

(73) Assignee: Italfarmaco SpA, Milan (IT)

( * ) Notice: Subject to any disclaimer, the term of this patent is extended or adjusted under 35 U.S.C. 154(b) by 154 days.

(21) Appl. No.: 12/662,004

(22) Filed: Mar. 26, 2010

(65) Prior Publication Data

US 2011/0237663 A1    Sep. 29, 2011

(51) Int. Cl.
*A01N 37/28* (2006.01)
*A61K 31/17* (2006.01)

(52) U.S. Cl. ........................... 514/575; 514/588
(58) Field of Classification Search .................. None
See application file for complete search history.

(56) References Cited

U.S. PATENT DOCUMENTS

2009/0088410 A1    4/2009 Zeldis

FOREIGN PATENT DOCUMENTS

| EP | 0 847 992 A1 | 6/1998 |
|---|---|---|
| WO | WO 93/07148 A1 | 4/1993 |
| WO | WO 97/43251 A1 | 11/1997 |
| WO | WO 9743251 A1 * | 11/1997 |
| WO | WO 02/22577 A2 | 3/2002 |
| WO | WO 02/30879 A2 | 4/2002 |
| WO | WO 03/076422 A1 | 9/2003 |
| WO | WO 2004/065355 A1 | 8/2004 |
| WO | WO 2004/069823 A1 | 8/2004 |
| WO | WO 2004/071400 A2 | 8/2004 |
| WO | WO 2004/092115 A2 | 10/2004 |
| WO | WO 2005/019174 A1 | 3/2005 |
| WO | WO 2006/003068 A2 | 1/2006 |
| WO | WO 2006/010750 A1 | 2/2006 |
| WO | WO 2006/063294 A2 | 6/2006 |
| WO | WO 2007/016354 A1 | 2/2007 |
| WO | WO 2007/067795 A2 | 6/2007 |
| WO | WO 2008/033747 A2 | 3/2008 |
| WO | WO 2008/058287 A1 | 5/2008 |
| WO | WO 2008/082646 A2 | 7/2008 |
| WO | WO 2010034693 A1 * | 4/2010 |

OTHER PUBLICATIONS

Mesa, New drugs for the treatment of myelofibrosis, Curr Hematol Malig Rep, Jan. 8, 2010, 5:15-20.*
Guerini et al., The histone deacetylase inhibitor ITF2357 selectively targets cells bearing JAK2V617F, Leukemia, 2007, 1-8.*
Mesa, How I treat symptomatic splenomegaly in patients with myelofibrosis, Blood, Mar. 30, 2000, 113: 5394-5400.*
Butler, L.M., et al; "Suberoylanilide Hydroxamic Acid, an Inhibitor of Histone Deacetylase, Suppresses the Growth of Prostate Cancer Cells in Vitro and in Vivo[1]"; *Cancer Research*; vol. 60; pp. 5165-5170 (2000).
Kralovics, R., et al; "A Gain-of-Function Mutation of JAK2 in Myeloproliferative Disorders"; *New England Journal of Medicine*; vol. 352; pp. 1779-1790 (2005).
Blanchard, F., et al; "Histone deacetylase inhibitors: new drugs for the treatment of inflammatory diseases?"; *Drug Discovery Today*; vol. 10, No. 3; pp. 197-204 (2005).
James, C., et al; "A unique clonal JAK2 mutation leading to constitutive signaling causes polycythaemia vera"; *Nature*; vol. 434; pp. 1144-1148 (2005).
Bi, G., et al; "The Molecular Mechanism of HDAC Inhibitors in Anticancer Effects"; *Cellular & Molecular Immunology*; vol. 3, No. 4; pp. 285-290 (2006).
Guerini, V., et al; "The histone deacetylase inhibitor ITF2357 selectively targets cells bearing mutated $JAK2^{V617F}$"; *Leukemia*; pp. 1-8 (2007).
Adcock, I.; "HDAC inhibitors as anti-inflammatory agents"; *British Journal of Pharmacology*; vol. 150; pp. 829-831 (2007).
Yoshida, M., et al; "Potent and Specific Inhibition of Mammalian Histone Deacetylase Both in Vivo and in Vitro by Trichostatin A"; *The Journal of Biological Chemistry*; vol. 265, No. 28; pp. 17174-17179 (1990).
Paris, M., et al; "Histone Deacetylase Inhibitors: From Bench to Clinic"; *Journal of Medicinal Chemistry*; vol. 51, No. 6; pp. 1505-1529 (2008).
Marks, P.A., et al; "Histone Deacetylase Inhibitors: Inducers of Differentiation or Apoptosis of Transformed Cells"; *Journal of the National Cancer Institute*; vol. 92, No. 15; pp. 1210-1216 (2000).
Richon, V.M., et al; "A class of hybrid polar inducers of transformed cell differentiation inhibits histone deacetylases"; *Proc. Natl. Acad. Science USA*; vol. 95; pp. 3003-3007 (1998).
Leoni, F., et al; "The Histone Deacetylase Inhibitor ITF2357 Reduces Production of Pro-Inflammatory Cytokines in Vitro and Systemic Inflammation in Vivo"; *Molecular Medicine*; vol. 11, No. 1-12; pp. 1-15 (2005).
Jones, P., et al; "A Novel Series of Potent and Selective Ketone Histone Deactylase Inhibitors with Antitumor Activity in Vivo"; *J. Med. Chem.*; vol. 51; pp. 2350-2353 (2008).
Zhou, N., et al; "Discovery of N-(2-Aminophenyl)-4-[(4-pyridin-3-ylprimidin-2-ylamino)methyl]benzamide (MGCD0103), an Orally Active Histone Deacetylase Inhibitor"; *J. Med. Chem.*; vol. 51; pp. 4072-4075 (2008).
Guerini, V., et al; "Selective Targeting of the $JAK2^{V617F}$ Mutation in Polycythemia Vera and Essential Thrombocythemia by ITF235, a Novel Histone Deacetylase Inhibitor"; *Blood* (ASH Annual Meeting Abstracts); 110: Abstract 555; 2 pgs (2007).
Guerini, V., et al; "Potent Inhibition of EEC Colony Formation in $JAK2^{V617F}$ PV and ET by Low Doses of ITF2357, a New Histone Deacetylase Inibitor"; *Blood*; vol. 108(11); Abst. 2702 (48th Annual Meeting Am. Soc. Hematol.); 2 pgs (2006).
Johansson, P., et al; "The effects of hydroxyurea on PRV-1 expression in patients with essential thrombocythemia and polycythemia Vera"; *Haematologica*; vol. 89; pp. 1264-1266 (2004).
Najean, Y., et al; "Treatment of Polycythemia Vera: The Use of Hydroxyurea and Pipobroman in 292 Patients Under the Age of 65 Years"; *Blood; American Society of Hematology*; vol. 90; pp. 3370-3377 (1997).

(Continued)

*Primary Examiner* — Sreeni Padmanabhan
*Assistant Examiner* — Svetlana M Ivanova
(74) *Attorney, Agent, or Firm* — Nixon & Vanderhye

(57) ABSTRACT

Method for treating Philadelphia-negative myeloproliferative syndromes in a patient in need of such treatment, by administering to the patient diethyl-[6-(4-hydroxycarbamoyl-phenylcarbamoyloxymethyl)-naphthalen-2-yl-methyl]-ammonium chloride or other pharmaceutically acceptable salts and/or solvates thereof, in combination with N-hydroxyurea.

16 Claims, No Drawings

OTHER PUBLICATIONS

Barosi, G., et al; "Response criteria for essential thrombocythemia and polycythemia vera: result of a European LeukemiaNet consensus conference"; *Blood; American Society of Hematology*; vol. 113; pp. 4829-4833 (2009).

Tutaeva, V., et al; "Application of PRV-1 mRNA expression level and JAK2V617F mutation for the differentiating between polycytemia vera and secondary erythrocytosis and assessment of treatment by interferon or hydroxyurea"; *Hematology*; vol. 12, No. 6; pp. 473-479 (2007).

Payne, J.E., et al; "Identification of KD5170: A novel mercaptoketone-based histone deacetylase inhibitor"; *Bioorganic & Medicinal Chemistry Letters*; 18; pp. 6093-6096 (2008).

Barbui, T., "How to manage children and young adults with myeloproliferative neoplasms"; *Leukemia*, pp. 1-6, doi: 10, 1038/leu. 2012.12, Jan. 18, 2012.

Bots, M., et al; "Rational Combinations Using HDAC Inhibitors"; *Clinical Cancer Research*; vol. 15, pp. 3970-3977, Published Online Jun. 9, 2009.

Chou, T-C., "Drug Combination Studies and Their Synergy Quantification Using the Chou-Talalay Method"; *Cancer Research*; vol. 70, pp. 440-446, Published Online First Jan. 12, 2010.

Chou, T-C., "Theoretical Basis, Experimental Design, and Computerized Simulation of Synergism and Antagonism in Drug Combination Studies[S]"; *Pharmacological Reviews*, vol. 58, pp. 621-681 (2006).

Chou, T-C; et al; "Quantitative Analysis of Dose-Effect Relationships: The Combined Effects of Multiple Drugs or Enzyme Inhibitors"; *Adv Enzyme Regul.*, vol. 22, pp. 27-55 (1984).

Federico, M., et al; "Histone Deacetylase Inhibitors in the Treatment of Hematological Malignancies and Solid Tumors"; *Journal of Biomedicine and Biotechnology*, vol. 2011, Article ID 475641, 12 pgs (2011).

Finazzi, G., et al; "Evidence and expertise in the management of polycythemia vera and essential thrombocythemia"; *Leukemia*, vol. 22, pp. 1494-1502 (2008).

Guerini, V., et al; "The histone deacetylase inhibitor ITF2357 selectively targets cells bearing mutated JAK2$^{V617F}$"; *Leukemia*, vol. 22, pp. 740-747 (2008).

Lemoine, M., et al; "Histone Deacetylase Inhibitors in the Treatment of Lymphoma"; *Discovery Medicine*, vol. 10, No. 54, pp. 462-470 (2010).

Leoni, F., et al; "The Histone Deacetylase Inhibitor ITF2357 Reduces Production of Pro-Inflammatory Cytokines In Vitro and Systemic Inflammation In Vivo"; *Molecular Medicine*, vol. 11, No. 1-12, pp. 1-15 (2005).

Miller, C.P., et al; "Therapeutic Strategies to Enhance the Anticancer Efficacy of Histone Deacetylase Inhibitors"; *Journal of Biomedicine and Biotechnology*; vol. 2011, Article ID 514261, 17 pgs. (2011).

Mithraprabhu, S., et al; "Deactylase inhibition in myeloproliferative neoplasms"; *Invest in New Drugs*, 28(Suppl), pp. S50-S-57 (2010).

Rambaldi, A., et al; "A pilot study of the Histone-Deacetylase inhibitor Givinostat in patients with JAK2V617F positive chronic myeloproliferative neoplasms"; *British Journal of Haematology*; vol. 150, pp. 446-455 (2010).

Reynolds, C. P., et al; "Evaluating Response to Antineoplastic Drug Combination in Tissue Culture Models"; *Methods in Molecular Medicine*, vol. 110 (Chemosensitivity 1: In Vitro Assays), pp. 173-183 (2005).

Thurn, K.T., et al; "Rational therapeutic combinations with histone deacetylase inhibitors for the treatment of cancer"; *Future Oncol.*, vol. 7, No. 2, pp. 263-283 (2011).

Vannucchi, A.M., et al; "Epigenetic therapy in myeloproliferative neoplasms: evidence and perspectives"; *J. Cell. Mol. Med.*, vol. 13, No. 8A, pp. 1437-1450 (2009).

* cited by examiner

METHOD FOR TREATING PHILADELPHIA-NEGATIVE MYELOPROLIFERATIVE SYNDROMES

Myeloproliferative syndromes are disorders of the neoplastic type which have in common the fact that they originate from pluripotent stem cells from bone marrow, that is to say, cells which, by dividing, can form various types of blood cell.

Myeloproliferative syndromes are separated into four types: chronic myeloid leukaemia (CML), polycythemia vera (PV), essential thrombocythemia (ET), and idiopathic myelofibrosis (IM).

The molecular basis for chronic myeloid leukaemia has been known for some time and consists in the formation of the Philadelphia chromosome, or the 9;22 translocation, and the generation of the BCR-ABL fusion gene; in these cases, called Philadelphia-positive myeloproliferative syndromes, the use of a specific ABL tyrosine kinase inhibitor (such as imitinib or desatinib) makes it possible to intervene selectively in the cells responsible for the pathology, limiting the possible consequences of a non-specific cytotoxicity to the detriment of the healthy cells.

For the other three pathologies, grouped under the name of Philadelphia-negative myeloproliferative syndromes, the molecular basis has been identified more recently [see, for example: Robert Kralovics et al. in *The New England Journal of Medicine* 352, 1779-1790 (2005); Chloé James et al. in *Nature* 434, 1144-1148 (2005)] and seems to relate to a single gene mutation, affecting JAK2 tyrosine kinase, with the generation of $JAK2^{V617F}$. In Europe, the incidence of Philadelphia-negative myeloproliferative syndromes is approximately 5 cases for every 100,000 inhabitants per year. For these syndromes, current therapy provides for the use of cytostatic drugs having a non-specific action, principally N-hydroxyurea (HU) or Pipobroman (Pi). Drug tolerance to these agents is often poor: leg ulcers and buccal aphthous ulcers (with HU) and gastric pain and diarrhea (with Pi) have been observed; furthermore, the risk of a thrombo-embolic event as well as the progression to myelofibrosis and/or leukemia is still present [see, for example: Yves Najean et al. in *Blood* 90, 3370-3377 (1997)]. Dosing for HU may be as high as 1-2.5 g/day; however, for patients which are particularly intolerant to HU, the dose regimen must be adjusted to obtain an acceptable low level of side effects. In most cases, therapeutic response at the tolerated doses of HU is less than satisfactory and a number of patients is refractory to N-hydroxyurea monotherapy.

It would therefore be important to identify new drugs or new combination protocols, to enhance the efficacy of current therapies and/or allow for their use at doses that are well tolerated.

As it is known in the art, histone deacetylases (HDACs) are enzymes capable of removing the acetyl group from lysine residues present in the N-terminal portion of histones or in other proteins.

HDACs can be divided into four classes, on the basis of structural homologies. Class I HDACs (HDAC 1, 2, 3 and 8) are similar to the RPD3 yeast protein and are located in the cell nucleus. Class II HDACs (HDAC 4, 5, 6, 7, 9 and 10) are similar to the HDA1 yeast protein and are located both in the nucleus and in the cytoplasm. Class III HDACs are a structurally distinct form of NAD-dependent enzymes correlated with the SIR2 yeast protein. Class IV (HDAC 11) consists of a single enzyme having particular structural characteristics. The catalytic site of HDACs of classes I, II and IV contains a zinc ion: HDAC activity can therefore be inhibited by various classes of molecule having in common the ability to bind zinc ions: e.g. hydroxamic acid derivatives, cyclic tetrapeptides, short-chain fatty acids, aminobenzamides, derivatives of electrophilic ketones, and the like. Class III HDACs are not inhibited by hydroxamic acids, and their inhibitors have structural characteristics different from those of the other classes.

The expression "histone deacetylase inhibitor" in relation to the present invention is to be understood as meaning any molecule of natural, recombinant or synthetic origin capable of inhibiting the activity of at least one of the enzymes classified as histone deacetylases of class I, class II or class IV.

Histone deacetylase inhibitors are a class of molecules provided with anti-neoplastic and anti-inflammatory activity.

In tumour cells, histone deacetylase inhibitors block cell proliferation and induce cell death and differentiation [Gaofeng Bi and Guosheng Jiang in *Cellular & Molecular Immunology* 3, 285-290 (2006)].

Histone deacetylase inhibitors are also capable of modulating the production of cytokines and other pro-inflammatory factors by immuno-competent cells and in vivo have demonstrated anti-inflammatory properties [Frédéric Blanchard and Céline Chipoy in *Drug Discovery Today* 10, 197-204 (2005); I M Adcock in *British Journal of Pharmacology* 150, 829-831 (2007)].

Several HDAC inhibitors are currently being tested for their clinical efficacy both in tumour pathologies and inflammatory ones [Marielle Paris et al. in *Journal of Medicinal Chemistry* 51, 1505-1529 (2008)].

Diethyl-[6-(4-hydroxycarbamoyl-phenylcarbamoyloxymethyl)-naphthalen-2-yl methyl]-ammonium chloride, which is described in WO 97/43251 (anhydrous form) and in WO 2004/065355 (monohydrate, crystal form), herein both incorporated by reference, is an HDAC inhibitor with anti-tumoral and anti-inflammatory activities; such an active principle, in the monohydrate crystal form, is also known as ITF2357 and/or Givinostat-hydrochloride-monohydrate.

Recently, it has been reported that sub-micromolar concentrations of ITF2357 inhibit the clonogenic activity of stem cells obtained from PV or ET patients and down-modulate the PVR-1 gene expression in granulocytes obtained from the peripheral blood of $JAK2^{V617F}$ PV patients [V. Guerini et al. *Leukemia* 22, 740-747 (2008)].

High level of PVR-1 gene expression may be a marker, together with the $JAK2^{V617F}$ mutation, of the presence of myeloproliferative diseases. IFN-α therapy in patients with PV is more effective then N-hydroxyurea treatment and significantly reduces increased PRV-1 expression [V. Tutaeva et al. *Hematology* 12, 473-479 (2007)].

Furthermore, N-hydroxyurea, at least in the early phase of treatment, has been shown to increase PRV-1 gene expression [P. Johansson et al. *Haematologica* 89, 1264-1266 (2004)].

DESCRIPTION OF THE INVENTION

We have now found, and this represents one aspect of the present invention, that the administration of diethyl-[6-(4-hydroxycarbamoyl-phenylcarbamoyloxymethyl)-naphthalen-2-yl methyl]-ammonium chloride or other pharmaceutically acceptable salts and/or solvates thereof, preferably in monohydrate form, more preferably in monohydrate crystal form, in combination with N-hydroxyurea, to patients suffering from myeloproliferative syndromes, preferably polycythemia vera, causes a significant amelioration of the clinical parameters compared to HU monotherapy.

An object of the present invention is therefore a method for treating Philadelphia-negative myeloproliferative syndromes which comprises administering diethyl-[6-(4-hydroxycarbamoyl-phenylcarbamoyloxymethyl)-naphthalen-2-yl-methyl]-ammonium in combination with N-hydroxyurea to a patient in need of such a treatment; preferably to a patient refractory to N-hydroxyurea monotherapy and/or whose therapeutic response to monotherapy with the same dose of N-hydroxyurea is unsatisfactory.

According to the invention, an "unsatisfactory response to N-hydroxyurea monotherapy" means a response that doesn't meet the european response criteria as defined in G. Barosi et al. *Blood* 113, 4829-4833 (2009), hereinafter incorporated by reference.

The Philadelphia-negative myeloproliferative syndrome is preferably polycythemia vera (PV) syndrome.

The diethyl-[6-(4-hydroxycarbamoyl-phenylcarbamoyloxymethyl)-naphthalen-2-yl methyl]-ammonium chloride or other pharmaceutically acceptable salts and/or solvates thereof, preferably in monohydrate form, more preferably in monohydrate crystal form in combination with N-hydroxyurea henceforth in this document is referred as the combination of the invention.

The combination of the invention is preferably administered to a patient on a daily basis.

Furthermore, diethyl-[6-(4-hydroxycarbamoyl-phenylcarbamoyloxymethyl)-naphthalen-2-yl methyl]-ammonium chloride and N-hydroxyurea may be administered to a patient simultaneously, separately or sequentially.

In particular, the combination of the invention is administered to a patient by enteral and/or parenteral route, preferably by oral, sublingual, rectal, intravascolar, intravenous, subcutaneous route, more preferably by oral route.

In more detail, diethyl-[6-(4-hydroxycarbamoyl-phenylcarbamoyloxymethyl)-naphthalen-2-yl-methyl]-ammonium chloride monohydrate of the invention is administered in an amount ranging from 10 to 150 mg per patient, preferably from 50 to 100 mg per patient, and the N-hydroxyurea of the invention is administered in an amount ranging from 100 to 1000 mg per patient, preferably of 500 mg per patient.

A further object of the present invention relates to a method for treating Philadelphia-negative myeloproliferative syndromes which comprises administering a formulation containing diethyl-[6-(4-hydroxycarbamoyl-phenylcarbamoyloxymethyl)-naphthalen-2-yl methyl]-ammonium chloride in combination with N-hydroxyurea and at least one physiologically acceptable excipient.

The formulation containing diethyl-[6-(4-hydroxycarbamoyl-phenylcarbamoyloxymethyl)-naphthalen-2-yl methyl]-ammonium chloride or other pharmaceutically acceptable salts and/or solvates thereof, preferably in monohydrate form, more preferably in monohydrate crystal form in combination with N-hydroxyurea and at least one physiologically acceptable excipient henceforth in this document is referred as the formulation of the invention.

The formulation of the invention is preferably administered to a patient on a daily basis and it preferably contains 10 to 150 mg of diethyl-[6-(4-hydroxycarbamoyl-phenylcarbamoyloxymethyl)-naphthalen-2-yl-methyl]-ammonium chloride monohydrate, preferably from 50 to 100 mg, and 100 to 1000 mg of N-hydroxyurea, preferably about 500 mg.

Furthermore, the formulation of the invention can be formulated in a solid or a liquid form. Preferably, said solid form is selected from tablet, granulate, microgranule or capsule and said liquid form is selected from a suspension or a solution.

Said formulation is administered to a patient refractory to N-hydroxyurea monotherapy and/or to a patient whose therapeutic response to monotherapy with the same dose of N-hydroxyurea is unsatisfactory.

The terms "treatment" and "treating", in relation to the present invention, are to be understood as meaning the action of caring for, relieving, mitigating, minimizing, eliminating or blocking the harmful effects resulting from the pathological state or the progression of the disease.

The following examples are intended to be illustrative of the invention rather than limiting the scope thereof.

Example 1

A multicentre, randomized, open-label, phase II study testing Givinostat-Hydrochloride-Monohydrate (ITF2357) in combination with N-hydroxyurea (HU) in Polycythemia Vera (PV).

Population in the study: 44 patients of both genders with an established diagnosis of JAK2$^{V617F}$ positive PV according to the revised WHO criteria, in need of cytoreductive therapy, non-responders to therapeutic doses of HU monotherapy for at least 3 months.

Duration of the treatment: up to a maximum of 24 weeks of continual administration.

Primary objective: To evaluate the efficacy of ITF2357 in combination with HU in patients with JAK2$^{V617F}$ positive Polycythemia Vera non-responders to therapeutic doses of HU in monotherapy.

Results: Patients response has been evaluated according to the european criteria [as reported in G. Barosi et al. *Blood* 113, 4829-4833 (2009)].

Examination of the preliminary data (6 patients) shows that the combined administration of ITF2357 (50 mg/day) and N-hydroxyurea (500 mg/day), to patients suffering from JAK2$^{V617F}$ positive polycythemia vera, produces a significant control of the clinico-hematologic parameters in patients that were refractory to the previous HU monotherapy.

The invention claimed is:

1. A method for treating Philadelphia-negative myeloproliferative syndromes in a patient in need of such treatment, which method comprises administering to said patient diethyl-[6-(4-hydroxycarbamoyl-phenylcarbamoyloxymethyl)-naphthalen-2-yl-methyl]-ammonium chloride or other pharmaceutically acceptable salts and/or solvates thereof in an amount ranging from 10 to 150 mg per patient, in combination with N-hydroxyurea in an amount ranging from 100 to 1000 mg per patient.

2. Method according to claim 1, wherein diethyl-[6-(4-hydroxycarbamoyl-phenylcarbamoyloxymethyl)-naphthalen-2-yl-methyl]-ammonium chloride is in monohydrate form.

3. Method according to claim 1, wherein diethyl-[6-(4-hydroxycarbamoyl-phenylcarbamoyloxymethyl)-naphthalen-2-yl-methyl]-ammonium chloride is in crystal form.

4. Method according to claim 1, wherein diethyl-[6-(4-hydroxycarbamoyl-phenylcarbamoyloxymethyl)-naphthalen-2-yl-methyl]-ammonium chloride and N-hydroxyurea are administered by oral route.

5. Method according to claim 1, wherein diethyl-[6-(4-hydroxycarbamoyl-phenylcarbamoyloxymethyl)-naphthalen-2-yl-methyl]-ammonium chloride and N-hydroxyurea are administered on a daily basis.

6. Method according to claim 1, wherein diethyl-[6-(4-hydroxycarbamoyl-phenylcarbamoyloxymethyl)-naphthalen-2-yl-methyl]-ammonium chloride and N-hydroxyurea are administered simultaneously, separately or sequentially.

7. Method according to claim 1, wherein diethyl-[6-(4-hydroxycarbamoyl-phenylcarbamoyloxymethyl)-naphthalen-2-yl-methyl]-ammonium chloride is administered in an amount ranging from 50 to 100 mg per patient and N-hydroxyurea is administered in an amount of 500 mg per patient.

8. Method according to claim 1, wherein said Philadelphia-negative myeloproliferative syndrome is selected from polycythemia vera, essential thrombocythemia, primary myelofibrosis or secondary myelofibrosis.

9. Method according to claim 1, wherein said Philadelphia-negative myeloproliferative syndrome is polycythemia vera.

10. Method according claim 1, wherein diethyl-[6-(4-hydroxycarbamoyl-phenylcarbamoyloxymethyl)-naphthalen-2-yl-methyl]-ammonium chloride and N-hydroxyurea are administered to a patient refractory to N-hydroxyurea monotherapy and/or to a patient whose therapeutic response to monotherapy with the same dose of N-hydroxyurea is unsatisfactory.

11. Method according to claim 1, which comprises administering a pharmaceutical formulation containing diethyl-[6-(4-hydroxycarbamoyl-phenylcarbamoyloxymethyl)-naphthalen-2-yl-methyl]-ammonium chloride or other pharmaceutically acceptable salts and/or solvates thereof, N-hydroxyurea and at least one physiologically acceptable excipient.

12. Method according to claim 11, wherein said formulation is in a solid or a liquid form.

13. Method according to claim 12, wherein said solid form is selected from tablet, granulate, microgranule or capsule.

14. Method according to claim 12, wherein said liquid form is selected from a suspension or a solution.

15. Method according to claim 11, wherein said formulation contains 10 to 150 mg of diethyl-[6-(4-hydroxycarbamoyl-phenylcarbamoyloxymethyl)-naphthalen-2-yl-methyl]-ammonium chloride monohydrate and 100 to 1000 mg of N-hydroxyurea.

16. Method according to claim 15, wherein said formulation contains 50 to 100 mg of diethyl-[6-(4-hydroxycarbamoyl-phenylcarbamoyloxymethyl)-naphthalen-2-yl-methyl]-ammonium chloride monohydrate and about 500 mg of N-hydroxyurea.

\* \* \* \* \*